(12) United States Patent
Jones

(10) Patent No.: US 6,948,537 B2
(45) Date of Patent: Sep. 27, 2005

(54) SYSTEMS AND METHODS FOR COLLECTING A PARTICULATE SUBSTANCE

(76) Inventor: John Jones, 11307 Paul Barwick Ct., San Diego, CA (US) 92126

( * ) Notice: Subject to any disclaimer, the term of this patent is extended or adjusted under 35 U.S.C. 154(b) by 0 days.

(21) Appl. No.: 10/160,148

(22) Filed: May 31, 2002

(65) Prior Publication Data

US 2005/0098228 A1     May 12, 2005

(51) Int. Cl.$^7$ ............................................. B65B 1/04
(52) U.S. Cl. ........................ 141/130; 422/99; 422/100
(58) Field of Search ....................... 141/130, 83, 95, 141/198, 98; 422/99, 100; 118/621, 712, 118/629

(56) References Cited

U.S. PATENT DOCUMENTS

| | | |
|---|---|---|
| 888,432 A | 5/1908 | Sutton et al. |
| 2,039,655 A | 5/1936 | Medenhall |
| 2,187,637 A | 1/1940 | Sutton et al. |
| 3,670,699 A | 6/1972 | Sargent ...................... 118/629 |
| 3,872,361 A | 3/1975 | Masuda ...................... 317/262 |
| 5,634,230 A | 6/1997 | Maurer ....................... 15/1.51 |
| 5,699,649 A | 12/1997 | Abrams et al. ............... 53/428 |
| 5,722,017 A | 2/1998 | Caruthers, Jr. et al. |
| 5,855,851 A | 1/1999 | Matsubara et al. |
| 5,858,099 A | 1/1999 | Sun et al. .................... 118/621 |
| 6,063,194 A | 5/2000 | Poliniak et al. ............. 118/623 |
| 6,076,216 A | 6/2000 | Biryukov ..................... 15/1.51 |
| 6,280,798 B1 | 8/2001 | Ring et al. ................... 427/459 |
| 6,287,595 B1 | 9/2001 | Loewy et al. ............... 424/457 |
| 6,295,194 B1 | 9/2001 | Sun et al. .................... 361/234 |
| 6,319,541 B1 | 11/2001 | Pletcher et al. ............ 427/2.14 |
| 6,551,558 B1 | 4/2003 | Mann et al. |

OTHER PUBLICATIONS

"The Crookes Tube and Related Experiments", no date.

*Primary Examiner*—Steven O. Douglas
(74) *Attorney, Agent, or Firm*—Procopio Cory Hargreaves & Savitch LLP

(57) ABSTRACT

A collector system for collecting a measurable amount of a particulate substance using an electrostatically charged collector. The collector is brought into proximity with the particulate substance and the electrostatic forces collect a measurable amount of the particulate substance on the collector. The collector system can further include a measurement system to measure the collected amount and a control system to adjust the collected amount until a specific amount of particulate substance is collected. The system can further include a conveyance system configured to convey a specific amount of the particulate substance from location to location within the collector system. In addition, the collector system can be configured to automatically collect and measure a specific amount of a particulate substance.

39 Claims, 6 Drawing Sheets

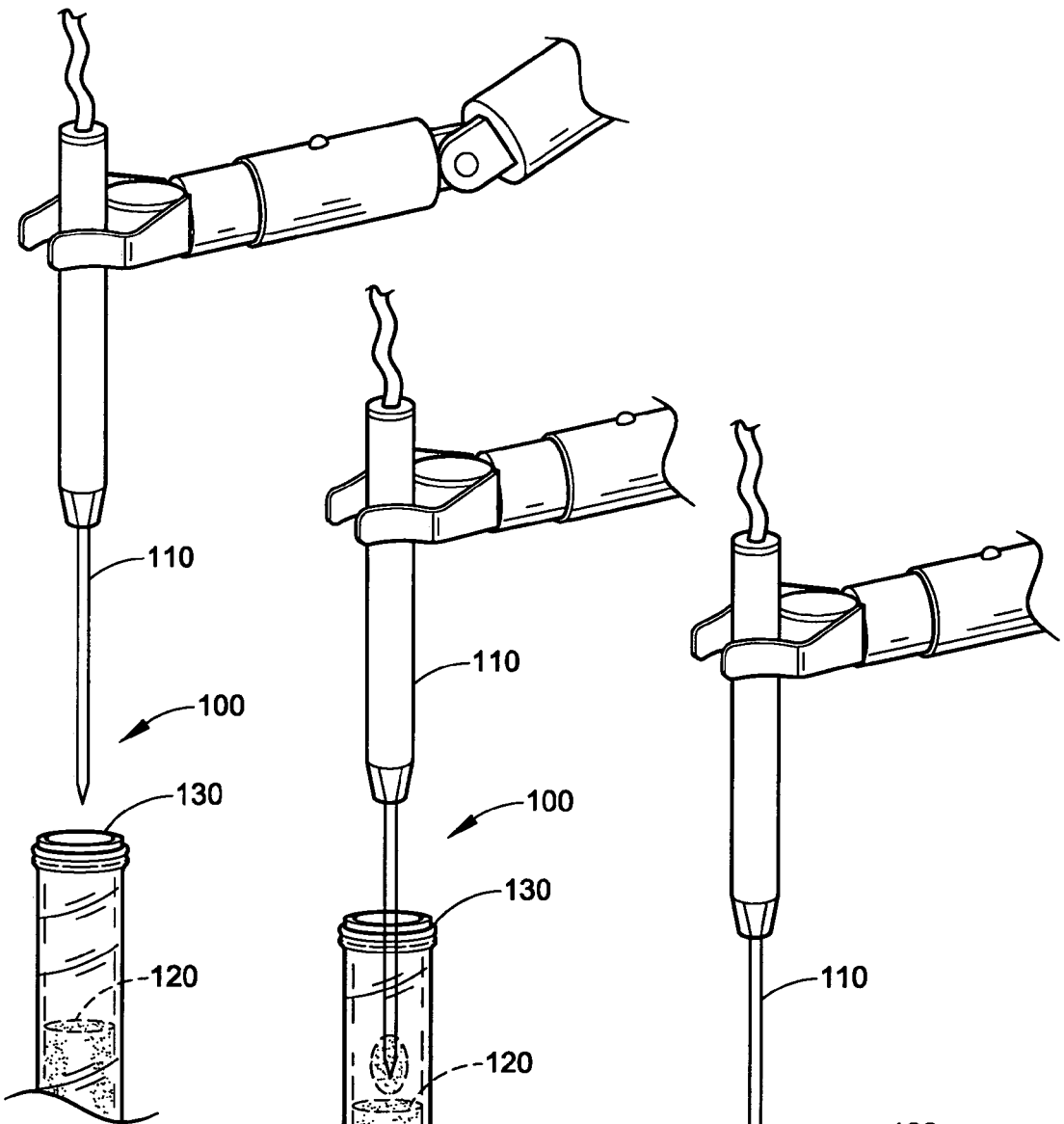
FIG. 6
FIG. 7
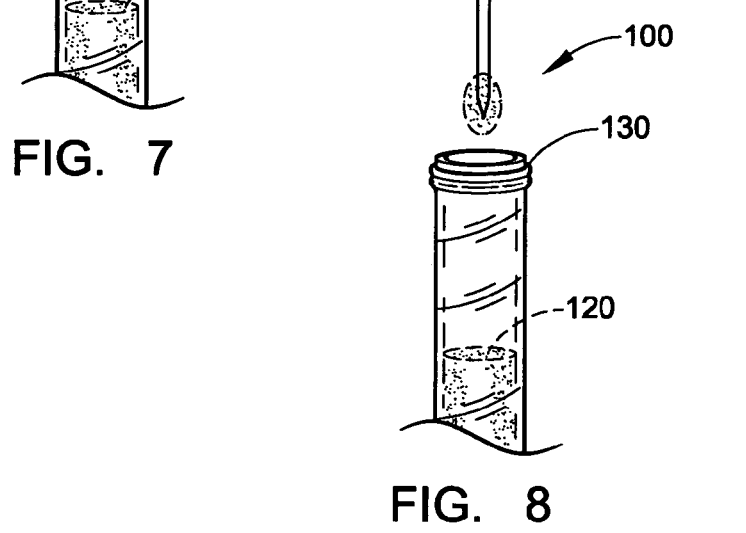
FIG. 8

SYSTEMS AND METHODS FOR COLLECTING A PARTICULATE SUBSTANCE

FIELD OF THE INVENTION

The present invention relates to collecting a particulate substance and more particularly, to collecting a measurable amount of a particulate substance using an electrostatically charged collector.

BACKGROUND INFORMATION

Many chemical substances are handled in powdered form. Chemicals in powdered form are generally more cost effective than liquids because they have a much longer shelf life than liquids and are less volatile than liquids, making them easier to ship and store. The powdered substances also provide the flexibility of solvating to any desired concentration. As a result, there is a need to measure and manipulate quantities of powdered or particulate substances. This need is present in many areas including the chemical, industrial, medical and pharmaceutical industries where process chemicals, industrial chemicals, medicines and drugs are generally stored in a powdered form. Specific quantities need to be isolated and measured for experimentation, processing and other uses. As a result, several different methods of collecting and measuring particulate substances have been developed.

One such method includes using mechanical vibrations to loosen the particulate substance to such an extent as to give it fluid-like characteristics, the particulate substance is then deposited into a receptacle where it can be isolated and measured. Another method includes using mechanical devices such as an Archimedes screw integrated into a special cap or special canister that has a mechanically operated valve. Yet another method for collecting the particulate substance includes using a vacuum tube system to collect the substance with suction or forced air motion.

These methods are costly to design, implement and operate because they require a great deal of manual preparation and cleaning between uses and are highly subject to the threat of cross contamination and/or the loss of valuable substances. Some of these methods are also unable to collect substances from typical laboratory storage containers. They require the use of =additional specially designed containers to accomplish the collection, which may also require the retooling of existing equipment. These methods are also unable to collect, isolate and measure particulate substances with the level of performance and efficiency, needed in most industries, such as where single aliquots from many different particulate substances are needed. In this case, the loss of particulate substances and the amount of time incurred in cleaning and reloading the equipment does not make these methods cost effective. The pharmaceutical industry, for instance, requires specific amounts of a particulate substance to be accurately measured to within a small tolerance, which is made more difficult because each of the many various substances have their own separate cohesive and adhesive physical characteristics. In fact, many of these methods are unable to outperform the typical lab technician collecting and measuring particulate substances manually.

SUMMARY

The systems and methods for collecting a particulate substance described herein include a collector system for collecting a measurable amount of a particulate substance using an electrostatically charged collector. The collector is brought into proximity with the particulate substance and the electrostatic forces collect a measurable amount of the particulate substance on the collector. The collector system can further include a measurement system to measure the collected amount and a control system to adjust the collected amount until a specific amount of particulate substance is collected. The system can further include a conveyance system configured to convey a specific amount of the particulate substance from location to location within the collector system. In addition, the collector system can be configured to automatically collect and measure a specific amount of a particulate substance.

The systems and methods described herein also include a method for collecting a specific amount of a particulate substance, including electrostatically charging a collector, bringing the charged collector into proximity with a particulate substance and collecting a measurable amount of the particulate substance on the charged collector. Also the method can further include measuring the amount of the collected particulate substance.

Other aspects, advantages, and novel features of the inventions will become apparent from the following Detailed Description, when considered in conjunction with the accompanying drawings.

BRIEF DESCRIPTION OF THE DRAWINGS

The details of the present invention, both as to its structure and operation, may be gleaned in part by study of the accompanying drawings, in which like reference numerals refer to like parts, and in which:

FIG. 6 is a schematic view illustrating another example collector assembly according to an embodiment of the present invention;

FIG. 7 is a schematic view illustrating another example collector assembly according to an embodiment of the present invention; and FIG. 8 is a schematic view illustrating another example collector assembly according to an embodiment of the present invention.

DETAILED DESCRIPTION

The systems and methods for collecting a particulate substance described herein enable the collection of a measurable amount of a particulate substance through the use of an electrostatically charged collector. The charged collector is placed within proximity of the particulate substance where the electrostatic forces attract and physically draw a measurable amount of substance to the collector and holds it in place. The collected particulate substance is then measured to determine if the desired amount has been collected. In this manner, the collection system collects, isolates and measures the particulate substance in a precise and accurate fashion, and satisfies the high tolerance needed by many industries.

Figure 1B:
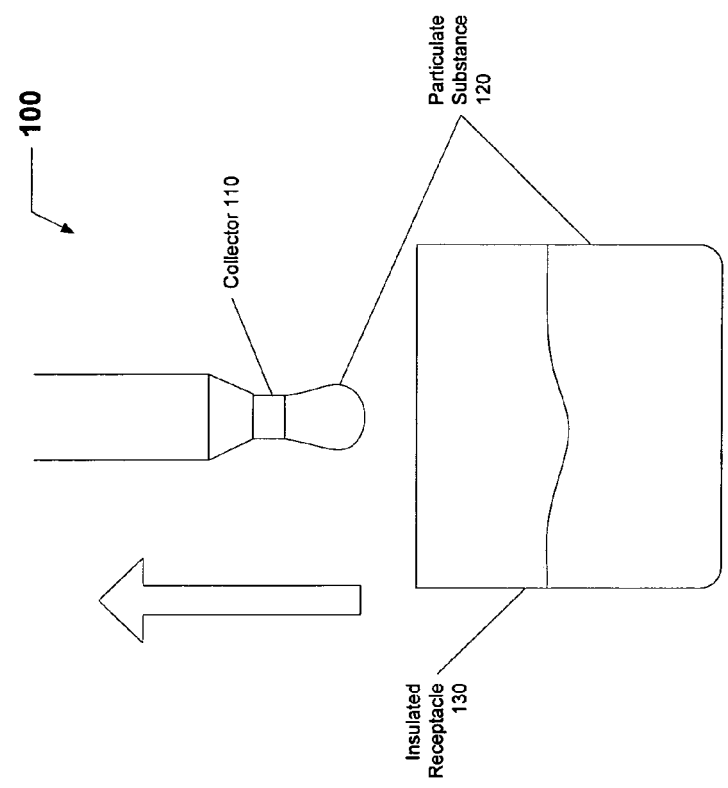
FIG. 1B is a block diagram illustrating an example collector assembly according to an embodiment of the present invention.
Figure 1A:
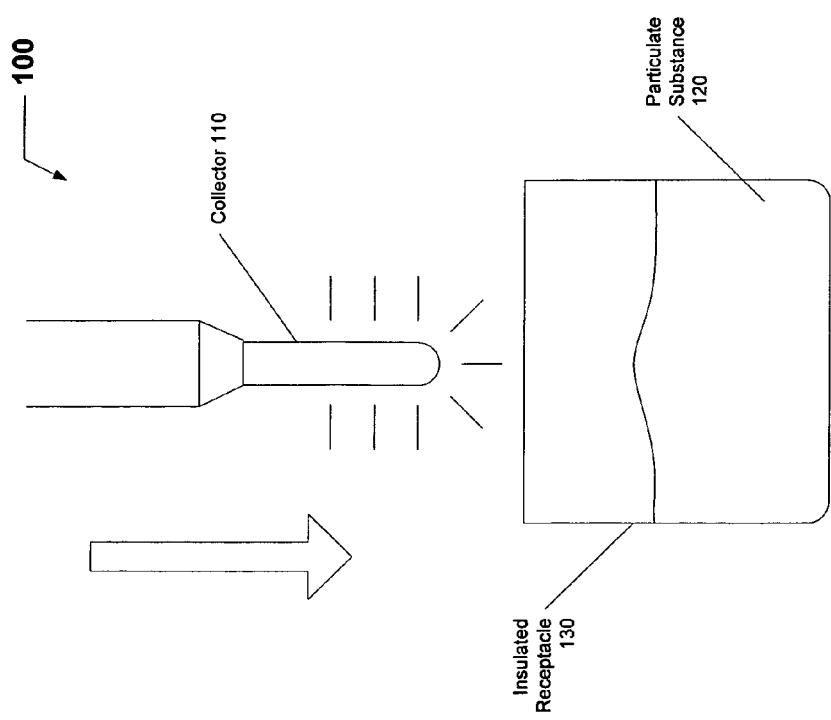
FIG. 1A is a block diagram illustrating an example collector assembly according to an embodiment of the present invention.

FIGS. 1A and 1B depict one embodiment of collection system 100 including electrostatically charged collector 110, particulate substance 120 and insulated receptacle 130. In FIG. 1A, electrostatically charged collector 110 is lowered (in the direction of the arrow) into proximity with particulate substance 120, contained within insulated receptacle 130. As the distance between collector 110 and particulate substance 120 decreases, the electrostatic force between collector 110 and particulate substance 120 increases until the attractive force is so great that a measurable amount of particulate substance 120 physically moves from insulated receptacle 130 to collector 110, where the electrostatic attraction continues to hold the collected particulate substance 120 in place. Collector 110 is within proximity of particulate substance 120 when collector 110 is at any location where a measurable amount of particulate substance 120 is collected. The proximity at which the measurable amount of particulate substance 120 is collected can be actual physical contact with particulate substance 120 or the proximity can be close to or near to particulate substance 120 without physical contact with particulate substance 120.

FIG. 1B depicts collector system 100 after a measurable amount of particulate substance 120 has been collected. Collector 110 is removed (in the direction of the arrow) from proximity with particulate substance 120 while the collected amount of particulate substance 120 remains held in place on collector 110 by the electrostatic force. Collector system 100 then deposits collected particulate substance 120 in a target receptacle.

In one embodiment, collected particulate substance 120 is deposited by lowering the electrostatic charge on collector 110 while positioned over a target receptacle. The charge is lowered to the extent that particulate substance 120 is no longer held to collector 110, depending on particulate substance 120 and the amount of charge needed to collect substance 120, this can include eliminating the charge on collector 110 altogether. In another embodiment, particulate substance 120 is deposited while collector 110 is within a target receptacle. Without the electrostatic charge to attract and hold particulate substance 120 to collector 110, collected particulate substance 120 falls from collector 110 into the target receptacle. In another embodiment, collected particulate substance 120 is deposited by physically vibrating collector 110 and jarring the collected particulate loose. In yet another embodiment, collected particulate substance 120 is deposited by air forced upon collector 110 and blowing the collected particulate substance 120 loose.

Collector 110 is electrostatically charged and there is no current moving through the collector other than the small amount that bleeds off into the surrounding air or onto particulate substance 120, insulated receptacle 130 or a target receptacle while in the collection or deposition process. Collector 110 is preferably metallic, however it can also be composed of plastic, ceramic and any other material capable of holding an electrostatic charge sufficient to collect particulate substance 120. In this embodiment, collector 110 is in the shape of a rod, which is preferable for the collection of various particulate substances 120. However, the shape of collector 110 is dependent on the physical characteristics of particulate substance 120 in addition to the actual quantity of particulate substance 120 desired to be collected, and is not limited to the rod shape depicted in FIGS. 1A and 1B. Increasing or decreasing the surface area of collector 110 will generally increase or decrease the amount of particulate substance 120 collected. Altering the surface area of collector 110 can be done either by altering the shape or the size of collector 110.

Collector 110 is readily interchangeable with another collector 110 and can easily be replaced or cleaned and reused, making it ideal for preventing cross contamination. In one embodiment, collector 110 is a spool of metallic wire, one portion of which is used to collect particulate substance 120. The portion of wire holding the collected particulate substance 120 can be detached and removed and a new portion of wire can be fed out of the spool where it can be used to collect another measurable amount of particulate substance 120. In this embodiment, a new collector 110 can be continuously fed from the spool each time particulate substance 120 is collected, and is therefore very effective in preventing cross contamination.

Particulate substance 120 can be any particulate substance capable of submitting to the electrostatic charge carried on collector 110. In general, particulate substance 120 is a dry loosely packed powdered or granular substance, comprised of particulates capable of attraction to the electrostatically charged collector 110.

Particulate substance 120 is not pre-charged in any manner before being collected by collector 110. The high electrostatic voltage placed on collector 110, induces an opposite charge on particulate substance 120, for example by polarization, and attracts the oppositely charged area of particulate substance 120. It is well known that the strength of an electrostatic force acting between two different bodies increases as the distance between the bodies decreases. Therefore, as charged collector 110 is brought closer to particulate substance 120, the electrostatic force acting upon particulates 120 grows in the strength, and eventually the electrostatic force physically draws particulates 120 to collector 110.

Insulated receptacle 130 is configured to hold particulate substance 120 and is composed of a non-conductive material. Receptacle 130 is isolated from ground to guard against potential arcing or other short circuiting that can occur when charged collector 110 is in proximity with receptacle 130. Insulated receptacle 130 can be any size enclosure such as a jar or tube or other non-conductive container, in which case particulate substance 120 is located within insulated receptacle 130. Receptacle 130 can also be a flat non-conductive surface without any sidewalls, such as a flat tray or dish, in which case particulate substance 120 is located on receptacle 130. For ease of discussion, insulated receptacle 130 is referred to as an enclosure in the description herein.

Figure 2:
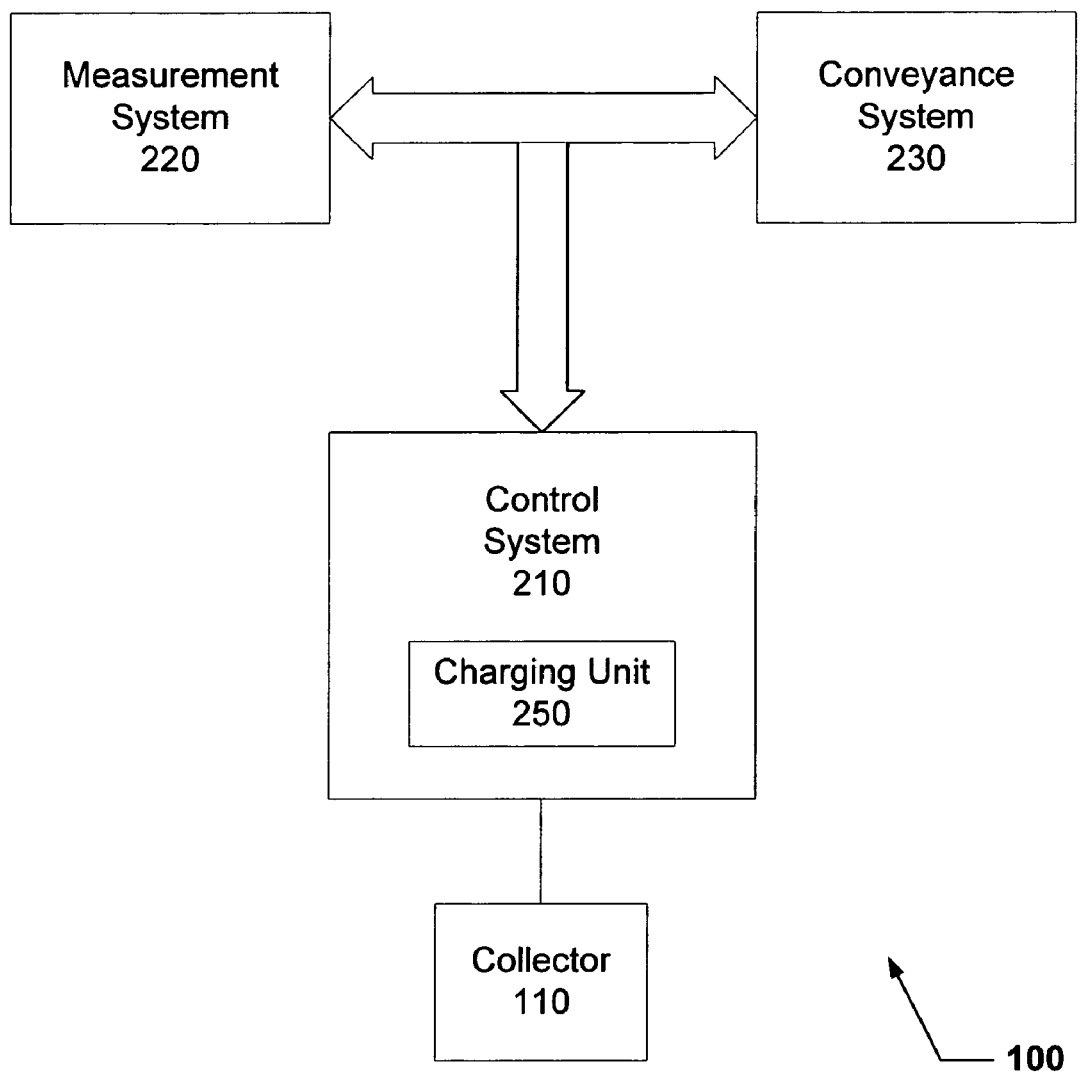
FIG. 2 is a block diagram illustrating an example collector assembly according to an embodiment of the present invention.

FIG. 2 depicts another embodiment of collection system 100 including collector 110, control system 210, measurement system 220, conveyance system 230 and communication channel 240. In this embodiment, control system 210 is communicatively coupled to measurement system 220 and conveyance system 230 via communication channel 240. In one embodiment, communication channel 240 is a central bus connecting control system 210, measurement system 220 and conveyance system 230. In another embodiment, communication channel 240 includes separate busses connecting each system 210, 220 and 230 together communication channel 240 is configured to allow communication between each of systems 210, 220 and 230.

Before describing this embodiment of collector system 100 in detail, it is useful to describe a simple example environment in which this embodiment can be implemented. One such example is a laboratory environment, where a lab technician needs to collect a specific amount of a chemical substance in powdered form. If numerous experiments are ongoing, the technician may need to make a large number of separate collections which could each vary by substance or amount. The lab technician uses collector system 100 to collect one or more samples, each containing a specific amount of the various chemical substances needed.

Collector system 100 is configured to collect a specific, measurable amount of particulate substance 120. This task is performed mainly by control system 210, which is configured to control measurement system 220, conveyance system 230 and collector 110. Control system 210 collects a measurable amount of particulate substance 120, measures the collected amount with measurement system 220, to ensure the specific amount was collected, and conveys the specific amount to a target location using conveyance system 230. Collector system 100 can be configured to perform all functionality automatically, without manual intervention.

The measurable amount of particulate substance 120 is an amount sufficient to be measured by measurement system 220. This amount is more than one or two particulates, and is generally no less than 0.1 mg. The measurable amount of particulate substance 120 is generally in the range of 1–20 milligrams (mg). This range is for illustration only and can vary beyond these limits dependent on the needs of the specific application. The upper limit of the range is dependent upon the amount of charge on the collector in addition to the amount of particulate substance 120 collected. The upper limit of the range may also be dependent on the physical and chemical characteristics of particulate substance 120, for example molecular size, atomic weight and the number of valence electrons as understood by those of ordinary skill in the art. When enough particulate substance 120 is collected the presence of the collected particulate substance 120 on collector 110 can prevent further collection.

The specific amount of particulate substance 120 is the amount collector system 100 needs to collect. This amount is within a range of amounts, or a tolerance, that is acceptable to the user or application. For instance, in the laboratory environment example, a lab technician may need to collect 1.2 mg of particulate substance 120. However, for the experiment the lab technician is conducting, any amount between 1.19 mg and 1.21 mg will suffice. This range of 1.19 mg to 1.21 mg is the specific amount of particulate substance 120. Therefore, if the collected amount is any amount in this range, then the collected amount is the specific amount needed. If the collected amount is not within this range, then it must be adjusted.

Control system 210 is configured to control the collection of particulate substance 120. Various embodiments may employ different means to achieve this function. One of these means includes varying the proximity of charged collector 110 to particulate substance 120 because less particulate substance 120 will be collected the further collector 110 is from particulate substance 120 within insulated receptacle 130. Conversely, more particulate substance 120 will be collected the closer collector 110 is to particulate substance 120 within insulated receptacle 130. Control system 210 can be configured to physically control the distance between collector 110 and particulate substance 120, and therefore control system 210 can control the collection of particulate substance 120.

In one embodiment, control system 210 collects particulate substance 120 by inserting collector 110 a predetermined distance into particulate substance 120 and then removing collector 110 from proximity. A measurable amount of particulate substance 120 is collected while collector 110 is in proximity with substance 120. The insertion and removal is done in a rapid manner and therefore allows the measurable amount of particulate substance 120 to be collected quickly.

Controlling the amount of time collector 110 is within proximity of particulate substance 120 is another means by which control system 210 can control the collection of particulate substance 120. The longer the amount of time control system 210 is in proximity with particulate substance 120, the more particulate substance 120 is collected.

Yet another means by which control system 210 controls the collection of particulate substance 120 is by varying the amount of charge on collector 110. The greater the charge on collector 110, the more particulate substance collector 110 will collect. Control system 210 includes charging unit 250, which is configured to create an electrostatic charge on collector 110. Charging unit 250 can be implemented as an electric generator, transformer, capacitor or other device capable of creating the electrostatic charge sufficient to collect a measurable amount of particulate substance 120.

In one embodiment, charging unit 250 is an inductive coil supplied by a direct current (DC) source in time pulses, the frequency of which can be used to control the charge applied to collector 110. In this embodiment, the collected particulate substance 120 can be deposited by varying the frequency and grounding insulated receptacle 130. However, because insulated receptacle 130 is preferably required to be isolated from ground, adequate care must be taken to avoid arcing or other shorting between charged collector 110 and ground.

By adjusting the charge applied by charging unit 250, control system 210 can control the collection of particulate substance 120. The amount of charge can be dependent on particulate substance 120 and the specific amount of particulate substance 120 to be collected in the individual application. Also, the charge can be dependent on the mass and density of the particulates within substance 120 and the amount of polarization that can be induced in the particulates within substance 120, as well as the triboelectric, adhesive and cohesive physical characteristics of particulate substance 120. In one embodiment, the electrostatic charge is on the order of +20 Kiloelectron Volts (KeV).

Control system 210 is further configured to adjust the collected amount until the specific amount is collected. Control system 210 can be configured to adjust the collected amount in multiple different ways depending upon the needs of the application. For instance, in one embodiment, measurement system 220 measures the collected amount before control system 210 removes collector 110 from proximity with particulate substance 120. If the collected amount is more than the specific amount, control system 210 causes collector 110 to deposit a portion of the collected amount. If the collected amount is less than the specific amount, control system 210 causes collector 110 to collect more of particulate substance 120.

In another embodiment, after collecting the measurable amount, control system 210 removes collector 110 from proximity and causes collector 110 to deposit the amount at measurement system 220, which measures the collected amount. If the collected amount is more than the specific amount, control system 210 causes collector 110 to collect a portion of the collected amount and removes it. If the collected amount is less than the specific amount, control system 110 causes collector 110 to collect an additional amount of particulate 120 and deposits it at measurement system 220. Measurement system 220 can then measure the adjusted amount a second time, and iteratively repeat the adjustment process until the specific amount is collected.

Control system 210 can be implemented as a software module executed by a microprocessor, Application Specific Integrated Circuit (ASIC) or as a System On Chip (SOC). Control system 210 can also be implemented as a general purpose computer or other hardware device whose function is to control the collection of particulate substance 120, measurement system 220, conveyance system 230 and charging unit 250.

Measurement system 220 measures the amount of particulate substance 120 collected. Measurement system 220 can measure the collected amount using multiple different methods. In one embodiment, measurement system 220 measures the amount of collected particulate substance 120 on collector 110 by using a scale coupled with collector 110. By knowing the weight of collector 110 with and without collected particulate substance 120, measurement system 220 can determine the weight of the collected particulate substance 120. In another embodiment, measurement system 220 measures the decrease in the amount of uncollected particulate substance 120 within receptacle 130 to determine the amount collected. In another embodiment, measurement system 220 measures the amount collected until the specific amount is collected.

In another embodiment, measurement system 220 uses algorithmic, extrapolatory and interpolatory techniques to determine the amount of collected substance 120 without a scale coupled to collector 110. By knowing the charge on collector 110, the proximity of collector 110, the amount of time collector 110 is in proximity with particulate substance 120, and the physical and electrical characteristics of substance 120, measurement system 220 can determine the amount of particulate substance 120 collected without the use of a scale. In another embodiment, control system 210 deposits the collected particulate substance 120 on a separate scale where measurement system 220 then measures the amount.

If the specific amount was collected, it is deposited in a target receptacle and is transferred out of collection system 100 by conveyance system 230, which then replaces it with another target receptacle if needed. Conveyance system 230 is configured to transfer insulated receptacle 130 and any particulate substance 120 to a target location. The target location can be a receptacle or any desired location, inside of or outside of collector system 100, based upon the needs of the specific application. Conveyance system 230 can be implemented as a conveyor belt apparatus, pick and place robotics or any other conveyance means configured to maximize the throughput of measurement system 220 and control system 210.

For instance, in one embodiment, conveyance system 230 transfers a target receptacle from a first scale operated by measurement system 220 to a second scale operated by measurement system 220. If, in one embodiment, multiple samples of particulate substance 120 need to be collected, conveyance system 230 physically moves the collected amounts out of collector system 100 and moves empty target receptacles within range of collector 110 to be filled. Conveyance system 230 can also be configured to maintain an adequate amount of particulate substance 120 within insulated receptacle 130, either by refilling it or by replacing insulated receptacle 130 with a filled one.

Measurement system 220 can be configured to measure the collected amount by proximity, time, charge or weight. When measurement system 220 is configured to measure by proximity, then measurement system 220 calculates the amount of substance 120 collected by measuring the proximity of collector 110 to substance 120. Measurement system 220 can use infrared, optical, electrical or mechanical measuring devices to determine the proximity of collector 110 to substance 120. By measuring the proximity and by knowing the amount of charge on collector 110, the amount of time collector 110 is within proximity and the physical characteristics of substance 120, measurement system 220 can determine the amount of substance 120 collected.

When measurement system 220 is configured to measure by time, then measurement system 220 calculates the amount of substance 120 collected by measuring the amount of time collector 110 is in proximity with substance 120. Measurement system 220 can use any clocking means capable of the level of precision and accuracy needed to make the measurement. By measuring the amount of time and by knowing the amount of charge on collector 110, the proximity of collector 110 with substance 120, measurement system 220 can determine the amount of substance 120 collected.

When measurement system 220 is configured to measure by charge, then measurement system 220 calculates the amount of substance 120 collected by measuring the amount of charge on collector 110 while in proximity with substance 120. Measurement system 220 can use any charge measuring means capable of the level of precision and accuracy needed to make the measurement. Measurement system 220 can be configured to measure the charge by measuring the frequency, voltage, current or power used by charging unit 250 to charge collector 110. By measuring the charge and by knowing the proximity of collector 110 with substance 120 and the amount of time collector 110 is in proximity with substance 120, measurement system 220 can determine the amount of substance 120 collected.

When measurement system 220 is configured to measure by weight, then measurement system 220 determines the amount of substance 120 collected by measuring the weight of substance 120 collected on collector 110 or remaining in insulated receptacle 130. Measurement system 220 can use any weight measuring means capable of the level of precision and accuracy needed to make the measurement. Measurement system 220 can be configured to measure the weight by using one or more scales depending on the needs of the application. For instance, in one embodiment, measuring system 220 uses two scales, a low precision scale and a slower, high precision scale. The collected substance 120 is deposited at the low precision scale for a quick low precision measurement, and if the collected amount is sufficiently close to the specific amount, collector 110 can make another collection while the collected amount is measured on a second high precision scale. This scale is slower because of the higher level of precision, but determines if the specific amount was collected with a higher level of certainty.

Measurement system 220 can also be configured to measure any combination of proximity, charge, time and weight to determine the collected amount of particulate substance 120. In one embodiment, measurement system 220 measures the amount of time collector 110 is in proximity with substance 120 and then deposits the collected amount at a high precision scale to verify that the specific amount was collected. In another embodiment, measurement system 220 measures the time, charge and proximity and also measures the amount of particulate substance 120 remaining in insulated receptacle 130 to determine if the specific amount was collected.

Figure 3:
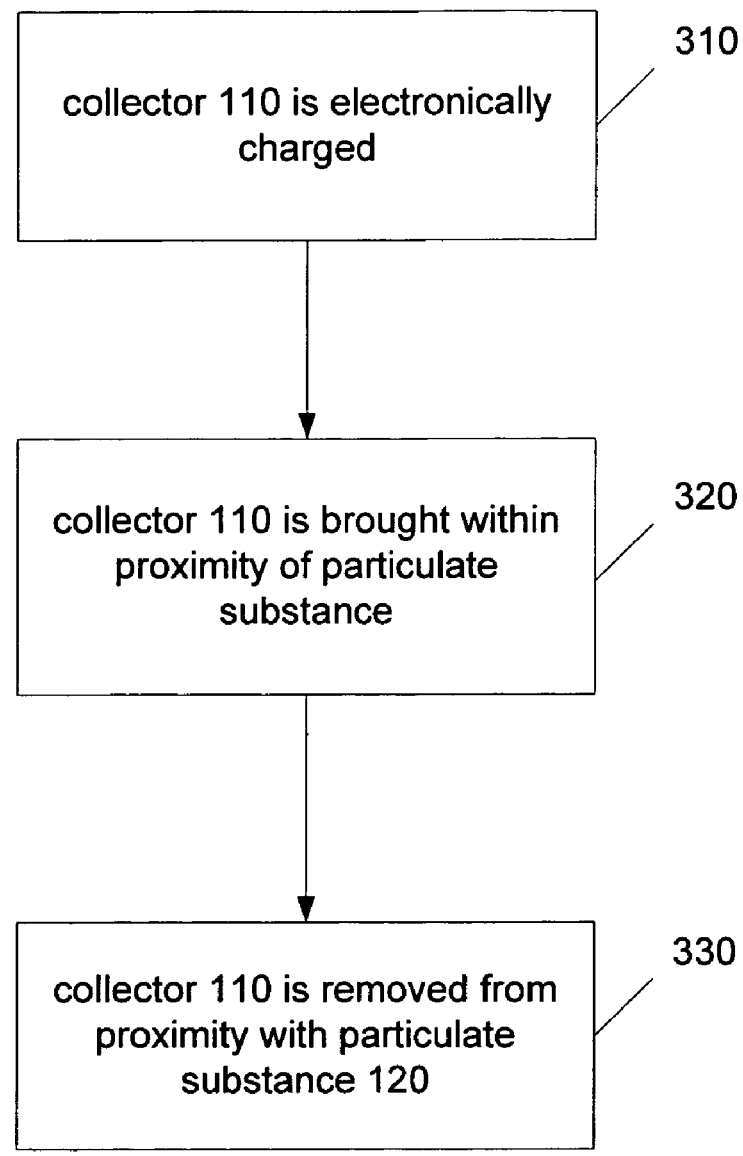
FIG. 3 is a flow diagram illustrating an example method for collecting a particulate substance according to an embodiment of the present invention.

FIG. 3 depicts one embodiment of a method for collecting a specific amount of particulate substance 120 using collector system 100. At 310, collector 110 is electrostatically charged. At 320, collector 110 is brought within proximity of particulate substance 120, which is located within receptacle 130. While within proximity of particulate substance 120, collector 110 collects a measurable amount of substance 120. At 330, collector 110 is removed from proximity with particulate substance 120.

Figure 4:
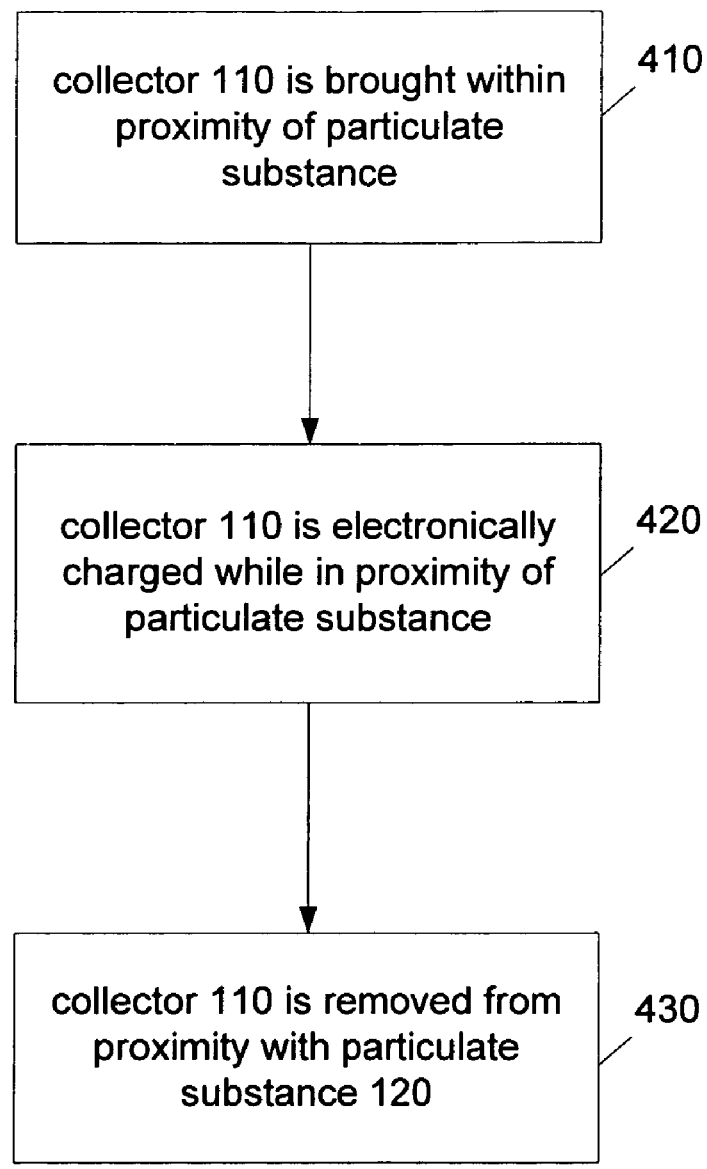
FIG. 4 is a flow diagram illustrating another example method for collecting a particulate substance according to an embodiment of the present invention.

FIG. 4 depicts another embodiment of a method for collecting a specific amount of particulate substance 120 using collector system 100. At 410, collector 110 is brought within proximity of particulate substance 120, which is located within receptacle 130. At 420, collector 1110 is electrostatically charged while in proximity of particulate substance 120. While within proximity of particulate substance 120, collector 110 collects a measurable amount of substance 120. At 430, collector 110 is removed from proximity with particulate substance 120, the collected amount held in place on collector 110 by the electrostatic charge.

Figure 5:
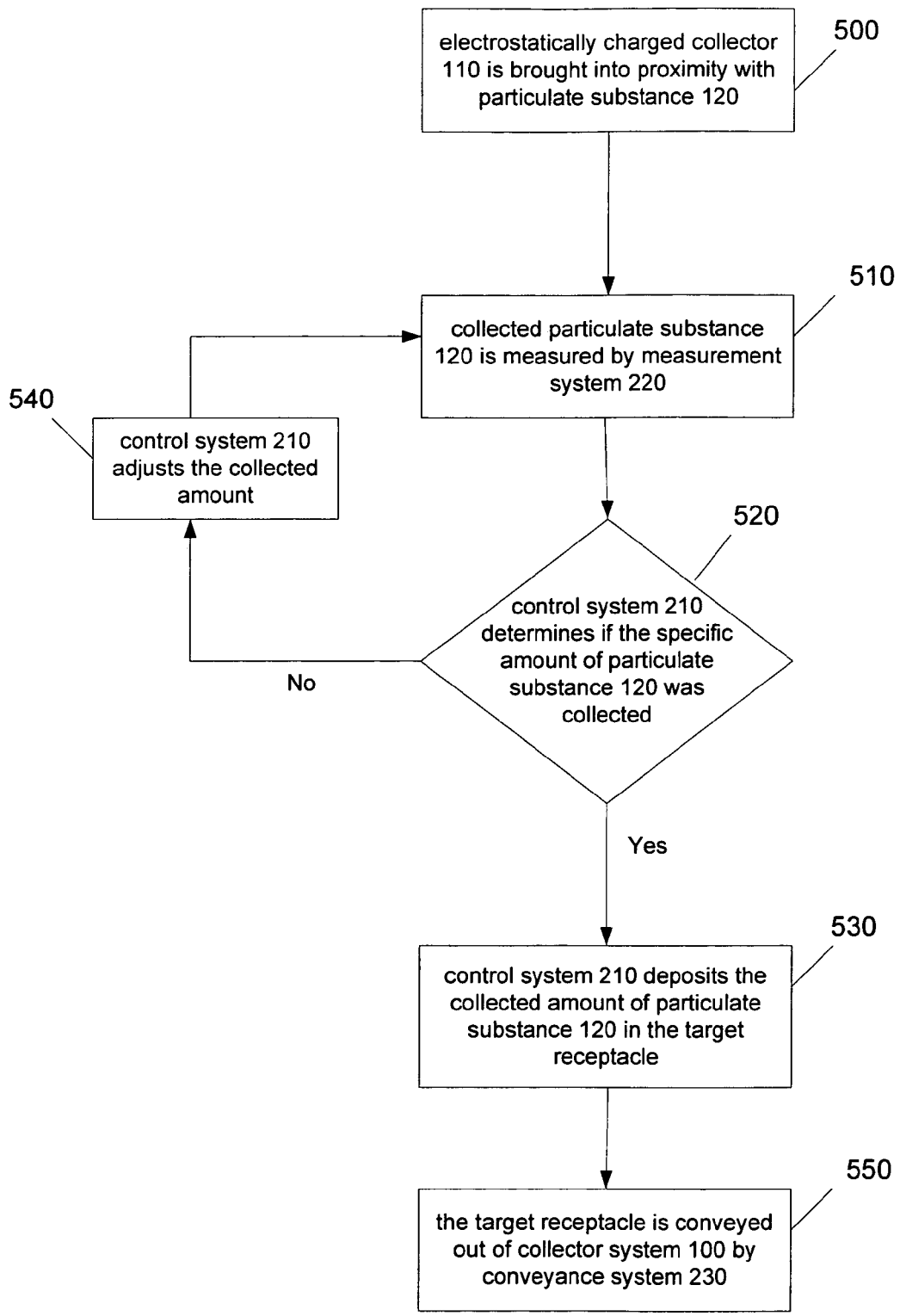
FIG. 5 is a flow diagram illustrating another example method for collecting a particulate substance according to an embodiment of the present invention.

FIG. 5 depicts one embodiment of a method for collecting a specific amount of particulate substance 120 using collector system 100. At 500, electrostatically charged collector 110 is brought into proximity with particulate substance 120, located within insulated receptacle 130, by control system 210. As a result of moving within proximity of particulate substance 120, electrostatically charged collector 110 collects a measurable amount of particulate substance 120. Then, at 510, the collected particulate substance 120 is measured by measurement system 220. At 520, control system 210 determines if the specific amount of particulate substance 120 was collected based upon the measurement from measurement system 220.

If the specific amount was collected, then, at 530, control system 210 deposits the collected amount of particulate substance 120 in the target receptacle. If the specific amount of particulate substance 120 was not collected, then, at 540, control system 210 adjusts the collected amount. After adjusting the amount, measurement system 220 measures the new collected amount at 310. The process repeats until the specific amount of particulate substance 120 is deposited at 330. At 550, the target receptacle is conveyed out of collector system 100 by conveyance system 230 for it's intended purpose.

FIGS. 6–8 depict an embodiment of collector system 100, according to the systems and methods described herein. FIG. 6 depicts collector 110 above insulated receptacle 130 containing particulate substance 120. In this embodiment, collector 110 is a metallic pin and insulated receptacle 130 is a glass vial, placed in an insulated stopper. FIG. 7 depicts charged collector 110 within proximity and physically contacting particulate substance 120. A measurable amount of particulate substance 120 is collected on the end of collector 110 by the electrostatic charge. FIG. 8 depicts charged collector 110 removed from insulated receptacle 130 with the collected particulate substance 120 held in place by the electrostatic charge.

Collector system 100 is described in the illustrated embodiment in FIGS. 6–8 in terms of an example laboratory environment. Description in these terms is provided for ease of discussion only. Accordingly, this example is not intended to limit the invention to particular applications.

While the particular systems and methods for collecting a particulate substance herein shown and described in detail is fully capable of attaining the above described objects of this invention, it is to be understood that the description and drawings presented herein represent a presently preferred embodiment of the invention and are therefore representative of the subject matter which is broadly contemplated by the present invention. It is further understood that the scope of the present invention fully encompasses other embodiments that may become obvious to those skilled in the art and that the scope of the present invention is accordingly limited by nothing other than the appended claims.

What is claimed is:

1. A method for collecting a specific amount of a particulate substance, comprising:
   electrostatically charging a collector;
   bringing the charged collector into proximity with a particulate substance;
   collecting an amount of the particulate substance on the charged collector; and
   measuring the amount of the uncollected particulate substance, wherein the decrease in the amount equals the collected amount.

2. The method of claim 1, further comprising measuring the amount of the collected particulate substance.

3. The method of claim 2, wherein measuring the amount comprises measuring the amount of the collected particulate substance until the specific amount is collected.

4. The method of claim 2, wherein measuring the amount comprises measuring the amount collected based upon the electrostatic charge, the proximity of the collector to the particulate substance and the time the particulate substance is in proximity with the collector.

5. The method of claim 2, further comprising:
   adjusting the amount of the collected particulate substance; and
   measuring the amount of the adjusted particulate substance, until the specific amount is collected.

6. The method of claim 1, further comprising depositing the collected particulate substance.

7. The method of claim 6, wherein depositing the substance comprises depositing the collected particulate substance by reducing the electrostatic charge on the collector.

8. The method of claim 6, wherein depositing the substance comprises applying a mechanical vibration to the collected particulate substance.

9. The method of claim 6, wherein depositing the substance comprises applying forced air to the collected particulate substance.

10. The method of claim 1, further comprising conveying the specific amount of the particulate substance to a target location.

11. The method of claim 1, wherein collecting the particulate substance further comprises varying the electrostatic charge on the collector to adjust the amount of the particulate substance collected by the collector.

12. The method of claim 1, wherein collecting the particulate substance further comprises varying the proximity of the collector to the particulate substance to adjust the amount of the particulate substance collected by the collector.

13. The method of claim 1, wherein collecting the particulate substance further comprises varying the length of time the collector is in proximity with the particulate substance to adjust the amount of the particulate substance collected by the collector.

14. The method of claim 1, wherein collecting the particulate substance further comprises varying the electrostatic charge on the collector and the proximity of the collector to the particulate substance to adjust the amount of the particulate substance collected by the collector.

15. The method of claim 1, wherein collecting the particulate substance further comprises varying the electrostatic charge on the collector and the length of time the collector is in proximity with the particulate substance to adjust the amount of the particulate substance collected by the collector.

16. The method of claim 1, wherein collecting the particulate substance further comprises varying the proximity of the collector to the particulate substance and the length of time the collector is in proximity with the particulate substance to adjust the amount of the particulate substance collected by the collector.

17. The method of claim 1, wherein collecting the particulate substance further comprises varying the electrostatic charge on the collector, varying the proximity of the collector to the particulate substance and varying the length of time the collector is in proximity with the particulate substance to adjust the amount of the particulate substance collected by the collector.

18. A collector system for collecting a specific amount of a particulate substance, comprising:
   an electrostatically charged collector configured to collect a measurable amount of a particulate substance when brought into proximity with the particulate substance;
   a control system configured to control the collector;
   a measurement system configured to measure the amount of particulate substance collected; and
   a communication channel configured to communicatively couple the control system with the measurement system.

19. The system of claim 18, further comprising an insulated receptacle configured to hold the particulate substance.

20. The system of claim 18, wherein the control system is configured to adjust the amount of the collected particulate substance until a specific amount is collected.

21. The system of claim 18, wherein the control system is configured to control the electrostatic charge on the collector to adjust the amount of the particulate substance collected by the collector.

22. The system of claim 18, wherein the control system is configured to control the proximity of the collector to the particulate substance to adjust the amount of the particulate substance collected by the collector.

23. The system of claim 18, wherein the control system is configured to control the length of time the collector is in proximity with the particulate substance to adjust the amount of the particulate substance collected by the collector.

24. The system of claim 18, wherein the control system is configured to control the electrostatic charge on the collector and the proximity of the collector to the particulate substance to adjust the amount of the particulate substance collected by the collector.

25. The system of claim 18, wherein the control system is configured to control the length of time the collector is in proximity with the particulate substance to adjust the amount of the particulate substance collected by the collector.

26. The method of claim 18, wherein the control system is configured to control the proximity of the collector to the particulate substance and the length of time the collector is in proximity with the particulate substance to adjust the amount of the particulate substance collected by the collector.

27. The system of claim 18, wherein the control system comprises a charging unit configured to apply the electrostatic charge to the collector.

28. The system of claim 18, wherein the control system is configured to adjust the amount of the collected particulate substance and the measurement system is configured to measure the adjusted amount until the specific amount is collected.

29. The system of claim 18, wherein the measurement system is farther configured to measure the amount collected based upon the electrostatic charge on the collector, the proximity of the collector to the particulate substance and the time the particulate substance is in proximity with the collector.

30. The system of claim 18, further comprising a measurement system configured to measure the amount of uncollected particulate substance until the decrease in the amount of uncollected particulate substance equals a specific amount.

31. The system of claim 18, further comprising a conveyance system coupled with the communication channel, the conveyance system configured to convey a specific amount of the particulate substance out of the collector system.

32. The system of claim 18, further comprising a conveyance system coupled with the communication channel, the conveyance system configured to convey a collected amount of the particulate substance between the collector and the measurement system.

33. The collector system for collecting a specific amount of a particulate substance, comprising:
   means for collecting a measurable amount of a particulate substance;
   means for electrostatically charging the means for collecting;
   means for bringing the electrostatically charged means for collecting into proximity with the particulate substance; and
   means for measuring the amount of collected particulate substance.

34. The system of claim 33, further comprising means for measuring an amount of an uncollected particulate substance.

35. The system of claim 33, further comprising means for adjusting the amount of a collected particulate substance.

36. The system of claim 33, further comprising means for depositing a collected particulate substance.

37. The system of claim 33, further comprising means for conveying a specific amount of the particulate substance to a target location.

38. The system of claim 33, further comprising means for controlling the collector.

39. The system of claim 33, further comprising:
   means for controlling the collector;
   means for measuring an amount of a collected particulate substance;
   means for conveying a specific amount of the particulate substance to a target location; and
   means for communicating between the means for controlling, the means for measuring and the means for conveying.

* * * * *